United States Patent [19]
Sugiyama

[11] Patent Number: 5,203,207
[45] Date of Patent: Apr. 20, 1993

[54] RAINDROP SENSOR

[75] Inventor: Masanori Sugiyama, Nishio, Japan

[73] Assignee: Aisin Seiki K.K., Kariya, Japan

[21] Appl. No.: 603,497

[22] Filed: Oct. 26, 1990

[30] Foreign Application Priority Data

Oct. 26, 1989 [JP] Japan .................................. 1-279375
May 1, 1990 [JP] Japan .................................. 2-115417
Sep. 21, 1990 [JP] Japan .................................. 2-253058

[51] Int. Cl.⁵ .......................... G01N 1/14; G08B 21/00
[52] U.S. Cl. .................................. 73/170.17; 340/602
[58] Field of Search .............. 73/171, 599, 579, 24.01, 73/24.04, 29.01; 364/420; 340/580, 962, 582, 602

[56] References Cited

U.S. PATENT DOCUMENTS

4,461,178  7/1984  Chamuel .......................... 340/582 X
4,604,612  8/1986  Watkins et al. ....................... 73/599
4,652,745  3/1987  Zanardelli ....................... 340/602 X

FOREIGN PATENT DOCUMENTS

0040626  3/1983  Japan .................................. 340/602
0185339  10/1983  Japan .................................. 340/602
0084141  5/1984  Japan .................................. 340/602
0174931  9/1985  Japan .................................. 340/602

Primary Examiner—Michael T. Razavi
Assistant Examiner—Elizabeth L. Shopbell
Attorney, Agent, or Firm—Sughrue, Mion, Zinn, Macpeak & Seas

[57] ABSTRACT

A raindrop sensor attached to a plate such as a windshield of a car. A first piezoelectric element as an ultrasonic generator is fitted to the plate via a first coupler. The coupler fixes the first element in an inclined state by a predetermined angle relative to the plate. Thereby, elastic waves or ultrasonic waves from the first element are transmitted while being repeatedly reflected in the plate. A second piezoelectric element as an electro-acoustic transducer is fitted to the plate via a second coupler. The second element detects amplitude of the ultrasonic waves transmitted in the plate.

9 Claims, 9 Drawing Sheets

RAINDROP SENSOR

BACKGROUND OF THE INVENTION

1. Field of the Invention

This invention relates to raindrop sensors for detecting amount of raindrops attached to a plate.

2. Description of the Related Art

Japanese Laid Open Patent Publication No. 59-61752, which has been laid open to public inspection in 1984, discloses a raindrop sensor. As illustrated in FIG. 10, the sensor has a light emitter 52 and a light receiver 53 fixed to a front windshield 51 of a car. Light 57 radiated from the emitter 52 advances while making total reflection in the windshield 51, and gets in the receiver 53. If raindrops 56 are attached to the windshield 51, the light 57 is not totally reflected. Thus, the more the amount of the raindrops 56 is, the less the amount of the light 57 entering the receiver 53 is.

However, this sensor is easily affected by extraneous light, e.g. sunlight, illumination light or the like. Therefore, there is a problem that detection of the raindrops 56 is disabled when the extraneous light is very strong.

Japanese Laid Open Patent Publication No. 59-192651, which has been laid open to public inspection in 1984, discloses another raindrop sensor. As shown in FIG. 11, the sensor has an ultrasonic transmitter 54 and an ultrasonic receiver 55 secured to a front windshield 51 of a car. Ultrasonic waves 50 radiated from the transmitter 54 are reflected at a wall surface of the windshield 5 and go into the receiver 55 after a fixed time. When raindrops 56 are deposited on the windshield 51, the ultrasonic waves 50 become reflected at a boundary surface of the raindrops 56 relative to the air. Thereby, the transmission time of the ultrasonic waves 50 is made longer from the radiation by the transmitter 54 to the detection by the receiver 55.

However, the above sensor can detect only the raindrops 56 just under the transmitter 54 and the receiver 55. As a result, there arises a problem that many pairs of transmitter 54 and the receiver 55 are necessary in case the sensor detects raindrops over a large area such as a front windshield of a car.

Moreover, the transmission time of the ultrasonic waves 50 or time difference is very short from the radiation by the transmitter 54 to the detection by the receiver 55. Subsequently, there is caused another problem that an electric circuit is very complicated and large sized in order to measure the time difference.

SUMMARY OF THE INVENTION

In view of the above, it is an object of the invention to provide a raindrop sensor, with a simple electric circuit, that is free from influence by extraneous light, and that is capable of detecting raindrops over a large area.

In accordance with one preferred mode of the invention, there is provided a raindrop sensor disposed on a plate. Wave transmitting means is associated with the plate to radiate elastic waves thereinto. Holding means holds the wave transmitting means at a predetermined angle relative to the plate. Thus, the elastic waves are transmitted while being repeatedly reflected in the plate. Wave receiving means is associated with the plate to detect amplitude of the elastic waves transmitted in the plate.

BRIEF DESCRIPTION OF THE DRAWINGS

The subject matter of the invention may be better seen in reference to the following description taken in conjunction with the accompanying drawings, in which.

DETAILED DESCRIPTION OF THE PREFERRED EMBODIMENTS

Figure 1:
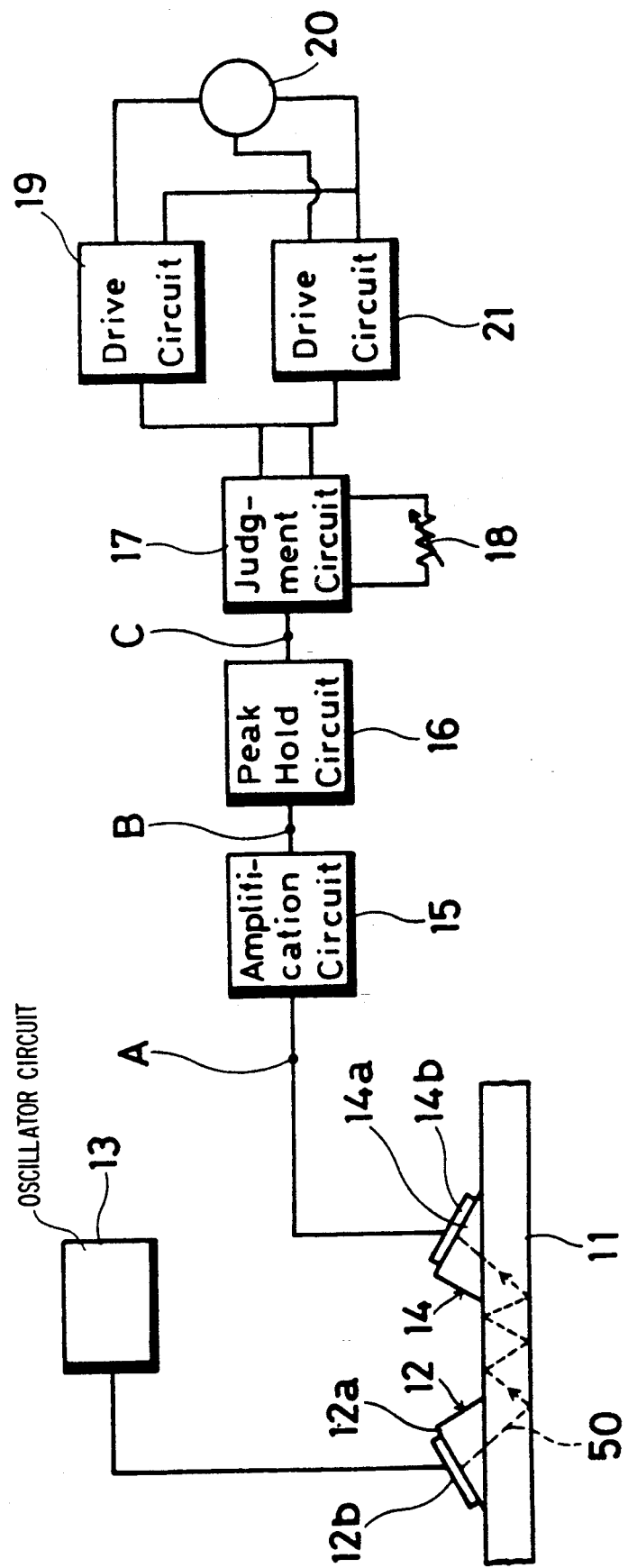
FIG. 1 is a block diagram showing a first embodiment of a raindrop sensor of the invention.

Referring to the drawings, wherein like reference characters designate like or corresponding parts throughout the several views, a first preferred mode of a raindrop sensor of the invention will be described hereafter. While the sensor of the invention may be used in any sensing applications for detecting raindrops on a plate, it will be specifically described in this embodiment in an application to detection of raindrops on a front windshield of a car.

Referring to FIG. 1, a wave sender 12 is fixed on a front window glass or windshield 11 of a car. Preferably, the wave sender 12 is composed of a coupler 12a and an ultrasonic generator such as a piezoelectric element 12b that is stuck on the coupler 12a.

An oscillator circuit 13 is electrically connected with the piezoelectric element 12b. The circuit 13 provides alternating current signals of about 1 to 10 Mhz or 100 Mhz so as to cause the element 12b to generate vibration of ultrasonic waves 50. The element 12b is vibrated mostly in its thickness direction with A.C. power supply from the oscillator 13. The element 12b is adapted to vibrate to radiate the ultrasonic waves 50 as elastic waves into the coupler 12a.

Figure 2:
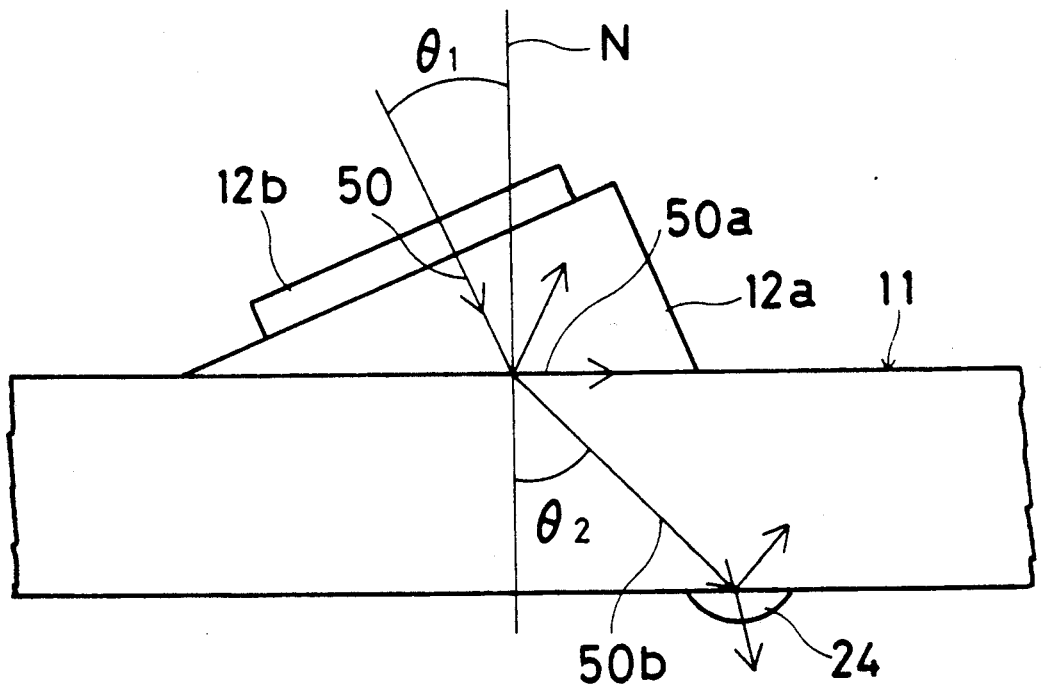
FIG. 2 is an enlarged sectional view of an example of a wave transmitter.

As illustrated in FIG. 2, the coupler 12a serves to hold the vibrator 12b in an inclined state by a predetermined angle $\theta1$ relative to a plane of the windshield 11. As a result, the ultrasonic waves 50 get into the windshield 11 with a predetermined incident angle $\theta1$ in relation to the normal N of the windshield 11.

The radiated ultrasonic waves 50 have a different sound speed in the window glass 11 from that in the coupler 12a, and are reflected and refracted at the boundary surface between the coupler 12a and the window 11. The incident waves 50 have their components of longitudinal waves 50a and transversal waves 50b separated at the time of refraction. In the present embodiment, the incident angle $\theta 1$ is so determined that the separated longitudinal waves 50a be radiated along the boundary surface between the coupler 12a and the windshield 11.

In case the incident angle $\theta 1$ is appropriately set, only the transversal waves 50b are radiated into the window 11. Here, if the transversal waves 50b enter the window 11 at a predetermined refractive angle $\theta 2$ relative to the normal N of the window 11, the radiated waves 50b are transmitted while being repeatedly reflected at a boundary surface of the window 11 and the air.

A desirous refractive angle $\theta 2$ is not less than about 40 degrees. Because the longitudinal waves 50a are hard to reflect at the boundary surface between the windshield 11 and the air with the refractive angle $\theta 2$ of 40 degrees or more. In other words, the windshield 11 functions as a filter to attenuate unnecessary longitudinal waves 50a where the angle $\theta 2$ is set in the above range.

The coupler 12a is made of an adequately selected material in order to satisfy the above incident angle $\theta 1$ and the refractive angle $\theta 2$. The material may preferably be, for example, lead, synthetic resin such as polyacetal resin, brass or the like. If the lead is used to make the coupler 12a, the incident angle is about 25 degrees, and the refractive angle $\theta 2$ is about 47 degrees. If the polyacetal resin is selected, the incident angle $\theta 1$ is about 25 degrees and the refractive angle $\theta 2$ is about 54 degrees.

Referring again to FIG. 1, a wave receiver 14 transforms the transmitted ultrasonic waves 50 into electric signals. Preferably, the wave receiver 14 is made of a coupler 14a and a piezoelectric element 14b, as an electro-acoustic transducer, fitted to the coupler 14a. It will be useful that the wave receiver 14 has the same structure as the wave sender 12.

The ultrasonic waves 50 getting into the receiver 14 vibrate the piezoelectric element 14b. Thus, the element 14b generates voltage in accordance with amplitude of the ultrasonic waves 50 transmitted thereto. An amplification circuit 15 amplifies the voltage outputted from the piezoelectric element 14b. A peak hold circuit 16 picks out a peak value of the amplified voltage. The peak hold circuit 16 outputs the peak voltage to a judgment circuit 17. Reflection characteristic of the transversal waves 50b are changed at portions of the windshield 11 where the raindrops 24, if any, are attached. Then, the transversal waves 50b leak out from these portions to the air. Thus, the amplitude of the waves 50b entering the receiver 14 is small when the amount of the attached raindrops 24 are big, and large when the amount is little.

Figure 3A:
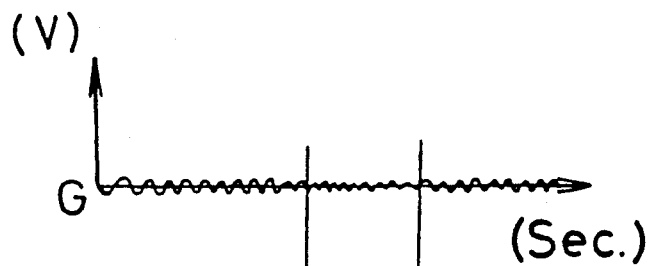
FIGS. 3a, 3b and 3c respectively show wave forms at points A, B and C of a circuit of FIG. 1.
Figure 3B:
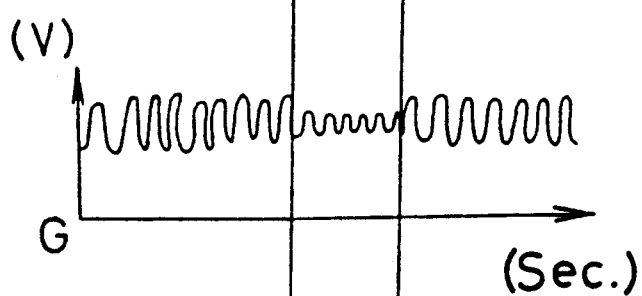
Figure 3C:
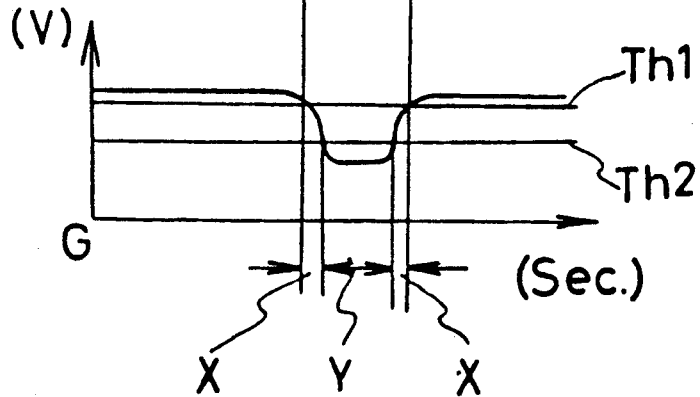
Figure 5:
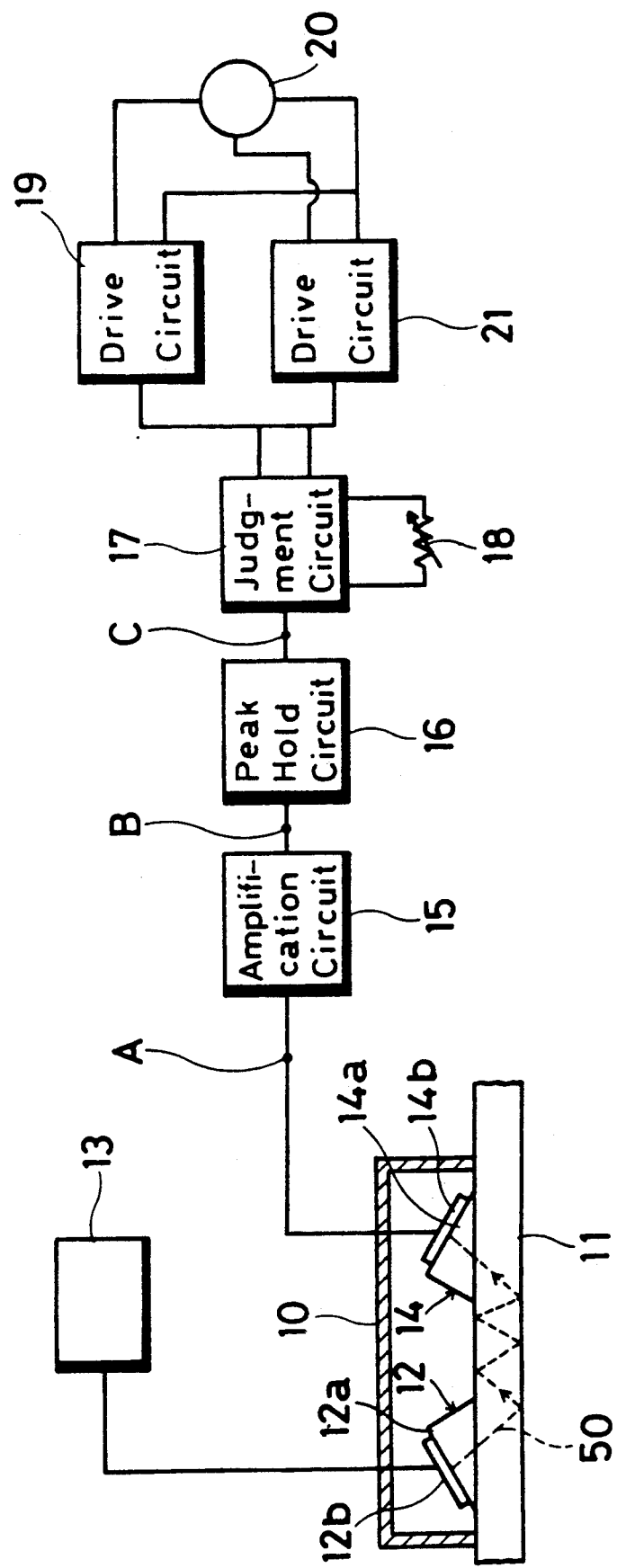
FIG. 5 is a block diagram showing a second embodiment of a raindrop sensor of the invention.

FIG. 3a shows waveforms of signals at a point A in the circuit, namely the signals outputted from the receiver 14. The receiver 14 outputs alternating current signals about the ground potential. A frequency of the A.C. signals is the same as a frequency of the transversal waves 50b radiated from the wave sender 12. Amplitude of the A.C. signals is inversely proportional to the amount of the raindrops 24 attached to the window 11. FIG. 3b shows waveforms of signals at a point B in the circuit, namely the signals outputted from the amplification circuit 15. The amplification circuit 15 amplifies the A.C. signals outputted from the receiver 14 so as to enlarge the amplitude thereof. The circuit 15 also applies a prescribed D.C. bias to the A.C. signals. FIG. 3c shows waveforms of signals at a point C in the circuit, namely the voltage outputted from the amplification circuit 15. The peak hold circuit 16 holds the peak values of the voltage from the amplification circuit 15 and outputs D.C. voltage in accordance with the amount of the raindrops 24 on the window 11.

The peak hold circuit 16 outputs the D.C. voltage into the judgment circuit 17. A variable resistor 18 is connected to the judgment circuit 17 for the purpose of setting sensitivities thereof. That is, the resister 18 determines a first reference value Th1 and a second reference value Th2 in order to judge the amount of the raindrops 24. The judgment circuit 17 compares the first and second reference values Th1 and Th2 with the D.C. voltage outputted from the peak hold circuit 16, thereby judging the amount of the raindrops 24 on the windshield 11. The judgment circuit 17 decides that, if the output voltage from the circuit 16 is higher than the first value Th1, there are no raindrops 24 on the window 11. The judgment circuit 17 judges that, if the output voltage is not lower than the first value Th1 but higher than the second value Th2, namely in the range of X in FIG. 3c, a small amount of the raindrops 24 are attached to the window 11. The judgment circuit 17 judges that if the output voltage is not higher than the second value Th2, namely in the range of Y in FIG. 3c, a large amount of the raindrops 24 are attached to the window 11.

When a small amount of the raindrops 24 are on the window 11, namely in the range of X, the judgment circuit 17 operates a low mode drive circuit 19. The low mode drive circuit 19 drives a wiper motor 20 at a normal speed to wipe the window 11. When a large amount of the raindrops 24 are on the window 11 namely in the range of Y, the judgment circuit 17 works a high mode drive circuit 20. The high mode drive circuit 21 drives the wiper motor 20 at a speed higher than the normal speed so as to rapidly wipe the window 11.

Figure 4:
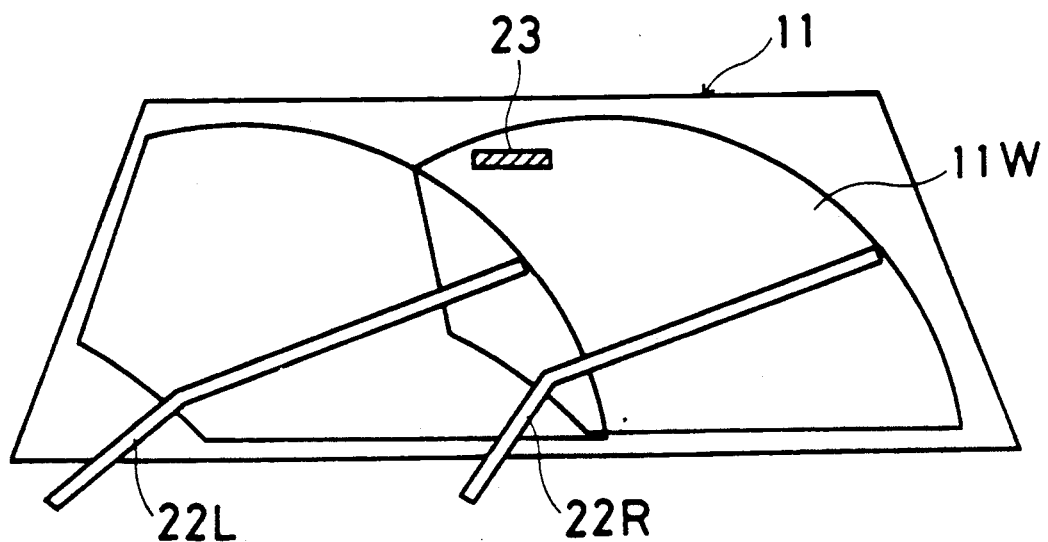
FIG. 4 is a plan view showing a detection area of raindrops on a windshield.

FIG. 4 illustrates a detection area 23 for the raindrops 24 on the windshield 11. The wave sender 12 and the wave receiver 14 are fixed at the rear surface of the windshield, that is, on a surface opposite to a wipe surface 11W of wipers 22L and 22R. Thereby, the raindrops 24 on the area 23 are cleared up in accordance with removing action of the wipers 22L and 22R. Subsequently, the wiper motor 20 is kept stopping until next detection of the raindrops 24. Thus, the wiper motor 20 is operated following the amount of the raindrops 24 on the windshield 11 In other words, the wipers 22L and 22R work suitably for view of a driver.

As described above, since the ultrasonic waves 50 are adopted to detect the raindrops 24, the sensor of this embodiment is free from any influences by extraneous light like sunlight or street light Moreover, if the windshield 11 is vibrated by, e.g., chatter of the wiper 22L, 22R, a frequency of the vibration is very much different from the ultrasonic frequency, so that the influence by the chatter can be disregarded.

The sender 12 and the receiver 14 never obstruct the wipers 22L and 22R, since they are fitted to the rear surface of the windshield 11. Therefore, the sensor of this embodiment is capable of maintaining stably its own characteristic for a long period of time.

The detection area 23 can be provided large enough between a pair of sender 12 and receiver 14 for the detection of the raindrops 24, since the ultrasonic waves 50 are transmitted, while being repeatedly reflected in the window 11, from the sender 12 to the receiver 14.

The response speed of the circuits 15, 16 and 17 can be low, since the detection of the raindrops 24 is carried out by use of the amplitude of the ultrasonic waves 50 that are detected by the receiver 14 Accordingly, the circuit 14, 15, 16 is able to have a simple structure and be small sized.

Figure 6:
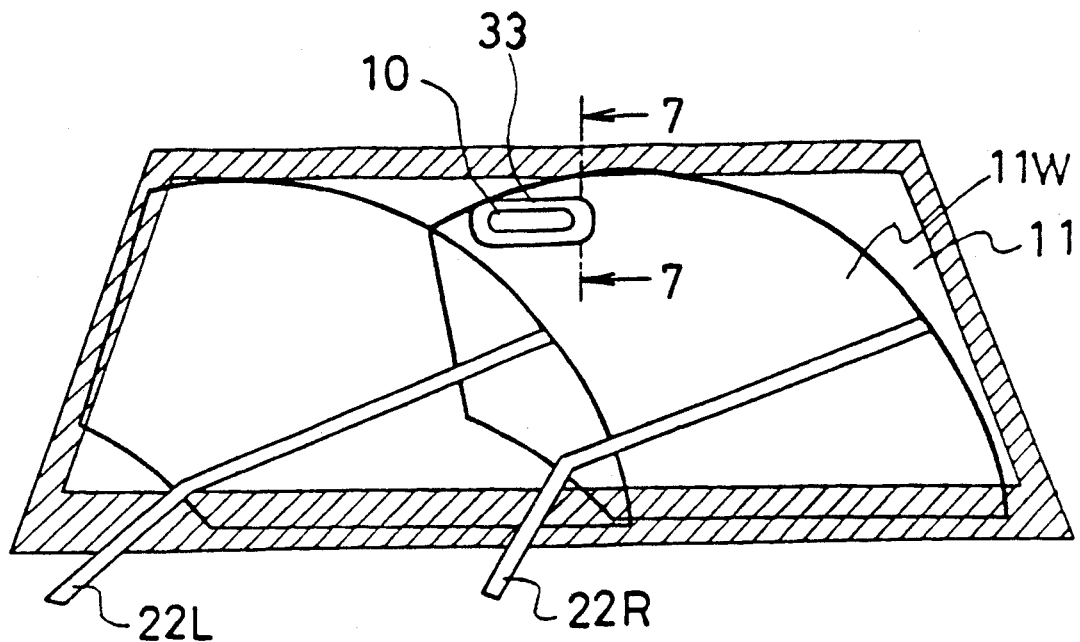
FIG. 6 is a plan view showing an arrangement of an example of a sensor unit on a windshield.
Figure 7:
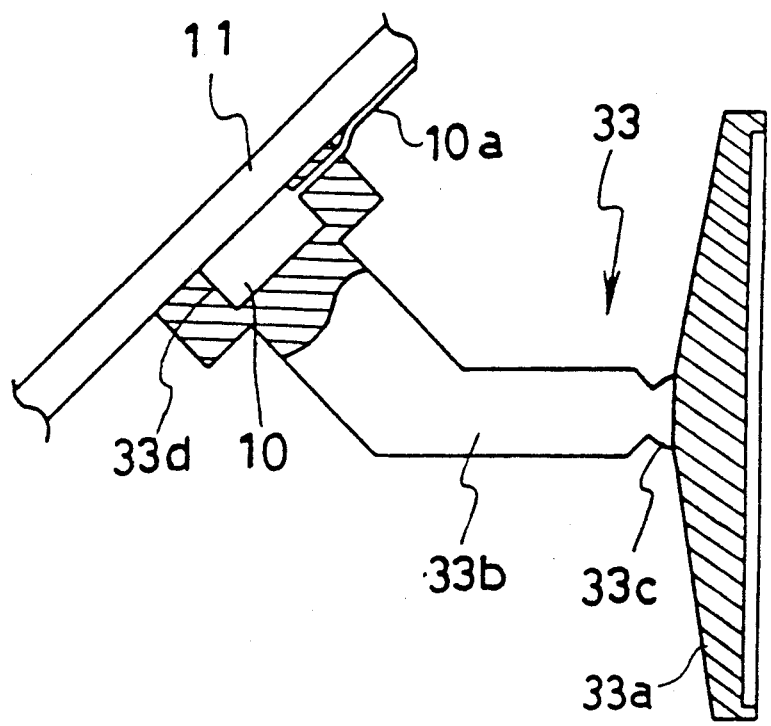
FIG. 7 is a sectional view taken along the line 7—7 of FIG. 6.

Next, a second embodiment of a raindrop sensor of the invention will be described hereafter Referring to FIGS. 6 and 7, a wave sender 12 and a wave receiver 14 are accommodated in a sensor unit 10 to make one body. The sensor unit 10 is secured between an inner mirror 33 and a windshield 11. The inner mirror 33 has a movable mirror body 33a and a stay 33b. The stay 33b is fitted to the windshield 11 via adhesive or the like. The movable mirror body 33a is attached to the stay 33b through a ball-and-socket joint 33c so as to be moved adjustably relative to the windshield 11. There is provided an inner space 33d in the stay 33b. The sensor unit 10 is fitted in the inner space 33d and detects an amount of raindrops 24 on the windshield 11. The sensor unit 10 is connected to an oscillator circuit 13, an amplification circuit 15, and so on via a conductor 10a.

With the sensor of this embodiment, the sensor unit 10 detects the raindrops 24 while being accommodated within the stay 33b, so that it never disturbs view of a person in a car. Moreover, there is little change in the appearance of the car by the provision of the sensor, and a high-grade impression of the car is not affected accordingly.

Figure 8:
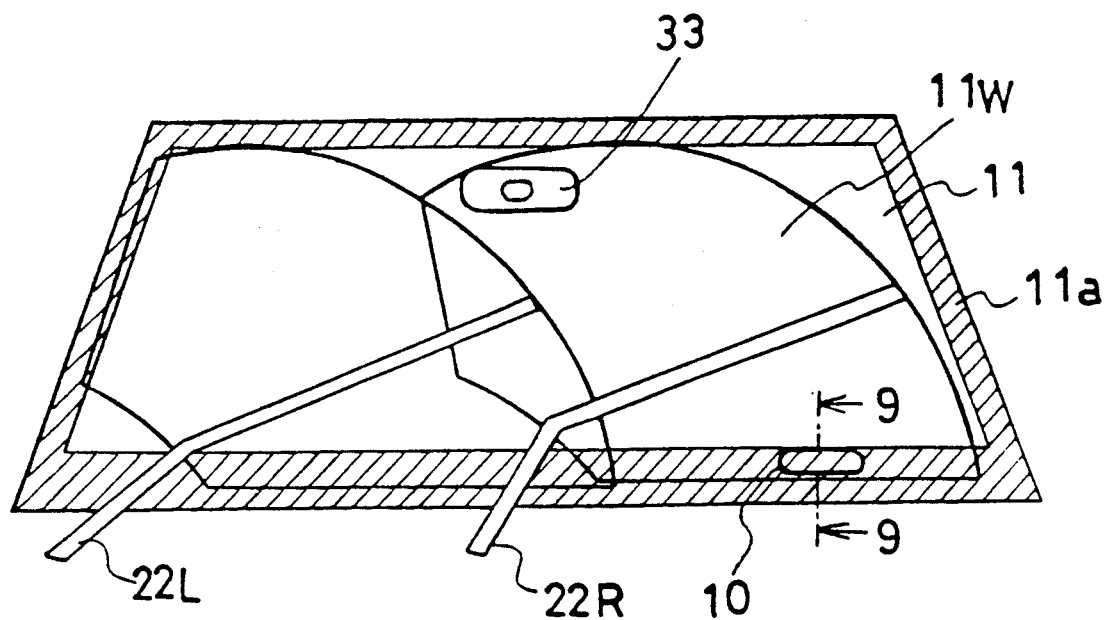
FIG. 8 is a plan view showing another arrangement of an example of a sensor unit on a windshield.
Figure 9:
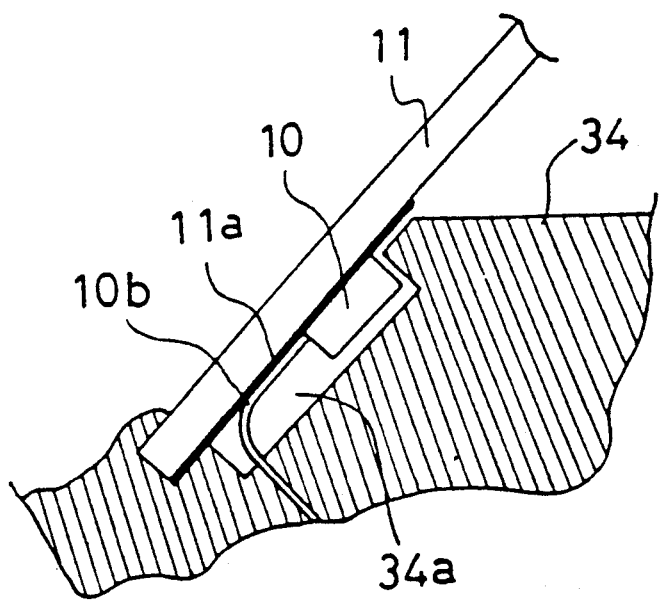
FIG. 9 is a sectional view taken along the line 9—9 of FIG. 8.
Figure 10:
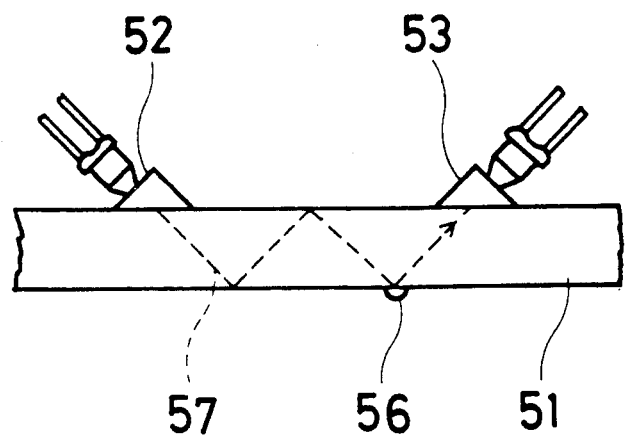
FIG. 10 is an enlarged fragmentary section showing a conventional raindrop sensor.
Figure 11:
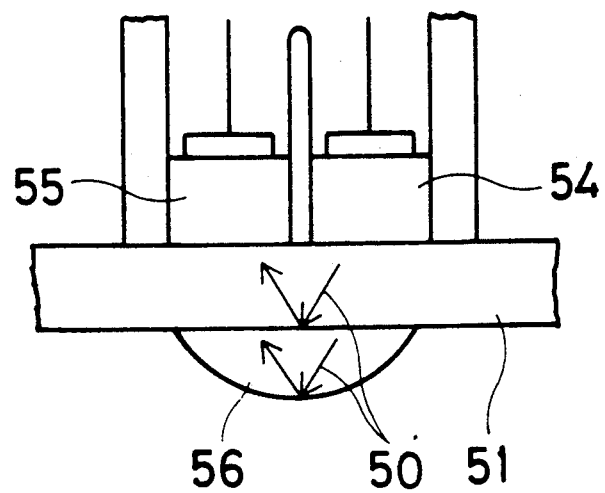
FIG. 11 is an enlarged fragmentary section showing another conventional raindrop sensor.

FIGS. 8 and 9 show a modification of an arrangement of the raindrop sensor on the windshield 11. In the figures, the sensor unit 10 is disposed on a black ceramic layer 11a which is formed on the windshield 11. The ceramic layer 11a is formed around the circumference of the windshield 11 in order to cover over a jointed area of the windshield 11 and a car body from outside the car. There is provided a chamber 34a between a dash board 34 and the windshield 11. The sensor unit 10 is accommodated in the chamber 34a and detects the amount of the raindrops 24. The sensor unit 10 is connected to the oscillator circuit 13, the amplification circuit 15, and so on through a conductor 10b.

With the above structure, the sensor unit 10 on the ceramic layer 11a can perform the detection work without interfering view from inside the car. Moreover, as in the case of FIGS. 6 and 7, a high-grade impression of the car is not lessened.

In the second embodiment, the sensor unit 10 is fixed on the rear surface of the window 11 or the surface opposite to a wipe surface 11W of the wipers 22L and 22R, like the first embodiment.

This invention may be practiced or embodied in still other ways without departing from the spirit and essential character thereof. For instance, while the raindrop sensor is attached to and detects the amount of the raindrops 24 on the front window 11 of the car in the illustrated preferred embodiments, the raindrop sensor may alternately be arranged on a rear window with a rear wiper of a car. Also, the raindrop sensor may be practiced in windows of another vehicles like trains, airplanes, ships, etc. That is, the raindrop sensor of the invention can be concretized in such various modes as to be provided on plates that need raindrop sensing, particularly all plates that have arrangements like wipers to remove raindrops and assure view.

Additionally, the wave sender 12 can have another form. For example, the ultrasonic generator may be a magnetostriction element, an electrostriction element, or the like other than the piezoelectric element 12b. Namely, the wave sender 12 may have any structures if it can generate ultrasonic waves as elastic waves and if it can set an incident angle and a refractive angle in such a desired range as transversal waves are able to advance while being repeatedly reflected in a plate. Similarly, the wave receiver 14 may have any structures if it can receive ultrasonic waves and transform amplitude thereof into electric signals. Accordingly, the wave receiver 14 can have a structure different from the wave sender 12.

Figure 12:
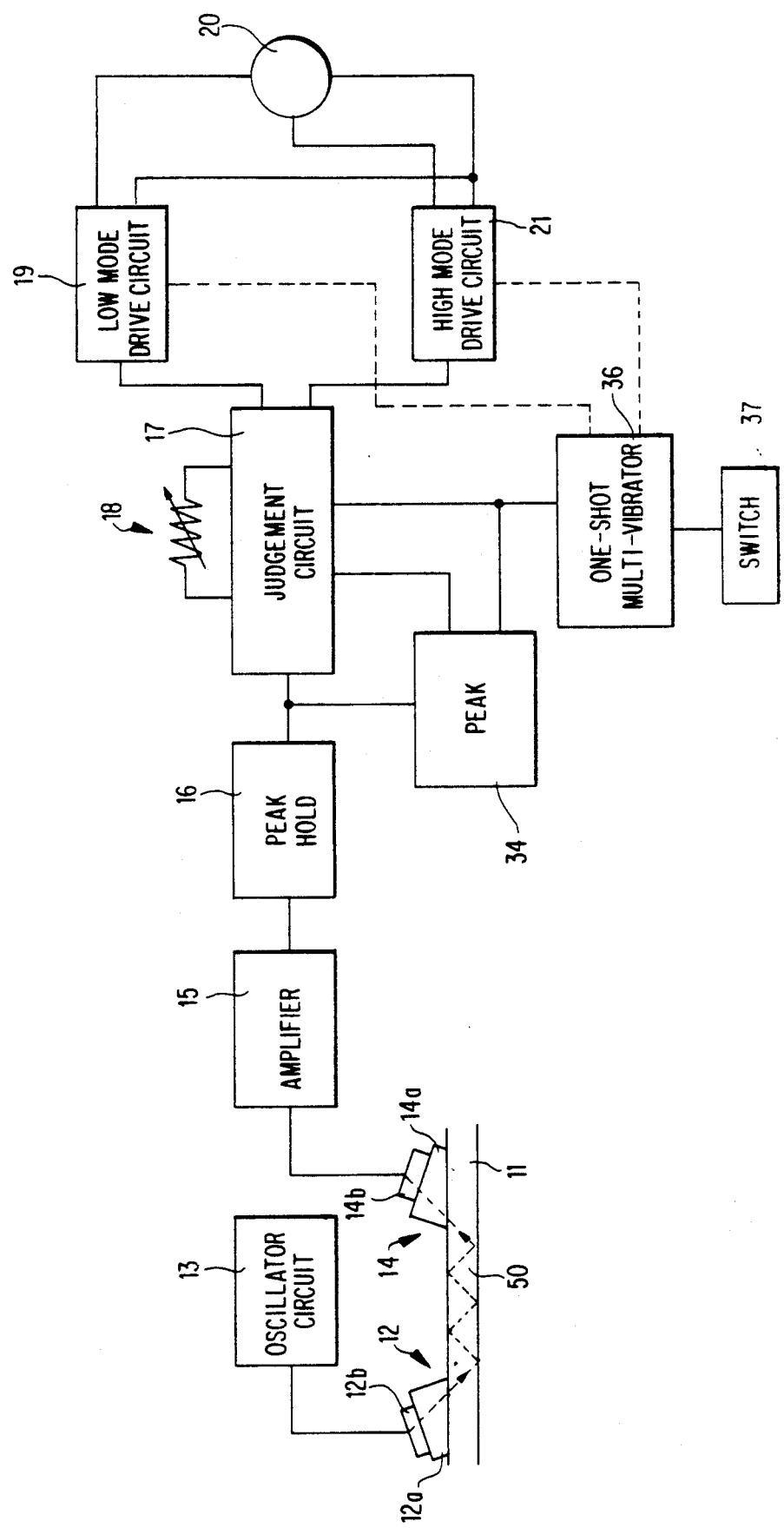
FIG. 12, is a block diagram showing a third embodiment of a raindrop sensor of the invention.
Figure 13:
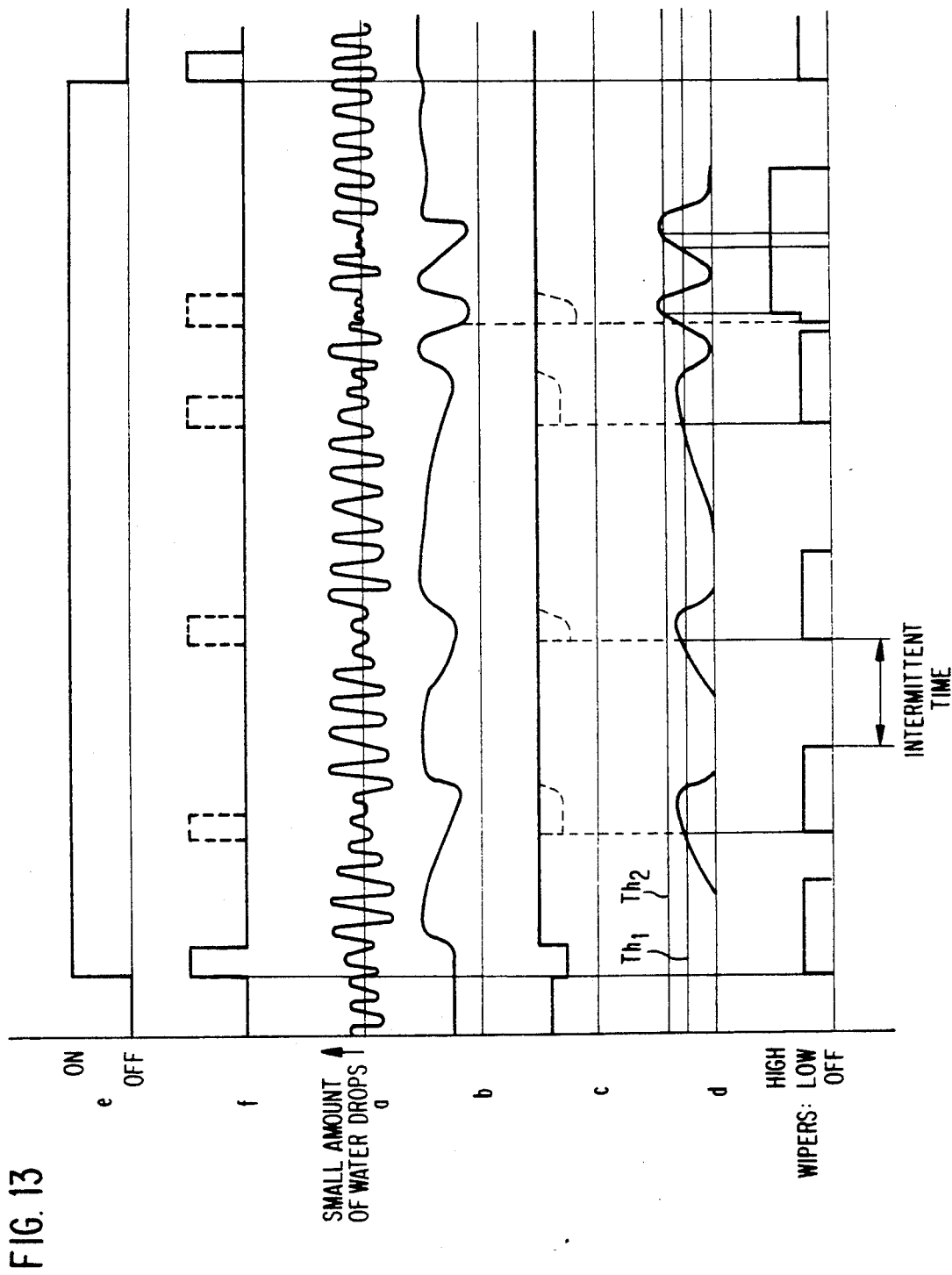
FIG. 13 is a graphical representation of various wave forms in the circuit of FIG. 12.

A third embodiment of a rain drop sensor according to the present invention will be described with reference to FIGS. 12 and 13. The receiver 14 is connected to the amplifier 15 so as to amplify the A.C. signal having the same frequency with the transversal waves and apply a direct bias to the resulting A.C. signal. The amplifier 15 is connected to the peak hold circuit 16 which is designed to output a D.C. voltage depending on the amount of water drops 24 on the windshield 14 which is indicated with a character of 'b' in FIG. 13 with holding the output signal from the amplifier 1115 or the amplified A.C. signal. Since this holding time is relatively short, the circuit 16 can be replaced with a low pass filter. The peak hold circuit 16 is connected to the judgment circuit 17 and another peak hold circuit 34. The circuit 34, which is designed to hold a signal for a relatively long time, stores or memorizes therein the output signal from the circuit 16 and outputs a D.C. signal which depends on the amount of water drops 24 assuming that the minimum water drops 24 indicated by a character 'c' in FIG. 13 on the windshield 14 is defined as a non-existence of water drops. The judgment circuit 17 has a variable resistor 18 for setting a first criteria Th1 and a second criteria Th2 both of which are used for judging the amount of water drops 24. In the judging circuit 17, the amount of water drops 24 is judged by comparing the first criteria Th1 (the second criteria Th2) with a deviation between output levels from both circuits 16 and 17. If the deviation is smaller than the first criteria Th1, it is considered that no amount of water drops 24 are on the windshield 11. If the deviation is larger than the first criteria Th1 and is smaller than the second criteria Th2, an amount of water drops is deemed to be on the windshield 11. If the deviation is greater than the second criteria Th2, a large amount of water drops 24 is deemed to be on the windshield 11.

The judgment circuit 17 is connected to the low mode drive circuit 19 and the high mode drive circuit 21 for driving the wiper motor 20 at a low speed and a high speed respectively. Also, via a switch 37, a one-shot multi-vibrator circuit 36 is connected to the judgment circuit 17 and the peak hold circuit 34. The circuit 36 is designed to provide a pulse signal as indicated with a character of 'f' in FIG. 13 when the switch is turned on or off indicated with a character of 'e' as shown in FIG. 13.

In operation of the foregoing embodiment, when the switch 37 is turned on, a single pulse signal is outputted from the one-shot multi-vibrator circuit 36. This signal actuates the low mode drive circuit 19, thereby turning on the motor 20 and resetting the output signal stored in the peak hold circuit 34 which is fed from the peak hold circuit 16. Thus, wiping operations of the wiper 22L and 22R are performed once and water drops 24 on the windshield are wiped away. Simultaneously, the peak hold circuit 16 provides an output signal which is at its peak value to the peak hold circuit 34 and is stored therein which results in the updating of the reference level. Thereafter, as water drops 24 increases on the windshield 11, the output level from the peak hold circuit 16 is lowered gradually, thereby increasing the deviation between the reference and the output level. If the deviation becomes larger than the first criteria Th1 and smaller than the second criteria Th2, the judgment circuit 17 begins to drive the low mode drive circuit 19 and the motor 20 is turned on at a normal speed which results in the wiping operation of the wipers 22L and 22R at a normal speed. If the deviation becomes greater than the second criteria Th2, the judgment circuit 17 brings the high mode drive circuit 21 into its operation, thereby driving the motor 20 at a high speed. Thus, water drops 24 on the windshield 11 are wiper away quickly by wipers 22R and 22L driven by the resulting motor 20. Due to the removal of water drops 24 from the windshield 11, the output level is increased, thereby lowering the deviation below the first criteria Th1. Then, the motor 20 is turned off. Thus, the wipers 22R and 22L are driven based on the visual condition of the driver since the rotating speed of motor 20, which drives the wipers, varies depending on the amount of water drops 24 on the windshield 11.

In the foregoing third embodiment, the output level stores in the peak hold circuit 34 is updated whenever the switch 37 is turned on, thereby enabling the accurate detection of the amount of water drops 24 without being affected by the variations of temperature, the voltage of the power supply and other factors. In addition, as shown in the dotted line in FIG. 12, feedback connections of the low mode drive circuit 20 and the high mode drive circuit 21 to the one-shot multi-vibrator circuit 36 enables the updating of the output level stored in the peak hold circuit 34 every time the wiper 22R (22L) is swung. This results in the accurate detection of water drops 24.

The preferred embodiments described herein are therefore illustrative and not restrictive, the scope of the invention being indicated in the appended claims and all variations which come within the meaning of the claims are intended to be embraced therein.

What is claimed is:

1. A raindrop sensor provided on a plate, comprising:
   wave transmitting means associated with a plate to radiate elastic waves thereinto;
   holding means for holding the wave transmitting means at a predetermined angle relative to the plate so that the elastic waves are transmitted while being repeatedly reflected in the plate; and
   wave receiving means associated with the plate to detect amplitude of the elastic waves transmitted in the plate;
   wherein the holding means is a coupler interposed between the plate and the wave transmitting means, the coupler holding the wave transmitting means relative to the plate so that the wave transmitting means has a predetermined incident angle in relation to a normal of the plate; and
   wherein the holding means is made of a material selected from the group consisting of lead, synthetic resin, zinc and brass.

2. A raindrop sensor according to claim 1, wherein the wave transmitting means radiates elastic waves into the plate at a predetermine incident angle through the holding means and said holding means is made of a material such that a refractive angle in the plate is substantially.

3. A raindrop sensor according to claim 1, wherein the holding means is made of the lead and the incident angle is set substantially in 25 degrees.

4. A raindrop sensor according to claim 1, wherein the holding means is made of a polyacetal resin and the incident angle is set substantially in 25 degrees.

5. A raindrop sensor provided on a plate, comprising:
   wave transmitting means associated with the plate to radiate elastic waves thereinto;
   holding means for holding the wave transmitting means at a predetermined angle relative to the plate so that the elastic waves are transmitted while being repeatedly reflected in the plate; and
   wave receiving means associated with the plate to detect amplitude of the elastic waves transmitted in the plate,
   wherein the wave transmitting means is a first piezoelectric element, the holding means is a first coupler interposed between the first piezoelectric element and the plate, the wave receiving means is a second piezoelectric element, and there is further provided a second coupler between the second piezoelectric element and the plate so as to hold the second piezoelectric element at substantially the same angle as the predetermined angle relative to the plate.

6. A raindrop sensor provided on a plate, comprising:
   wave transmitting means associated with the plate to radiate elastic waves thereinto;
   holding means for holding the wave transmitting means at a predetermined angle relative to the plate so that the elastic waves are transmitted while being repeatedly reflected in the plate;
   wave receiving means associated with the plate to detect amplitude of the elastic waves transmitted in the plate; and
   setting means for setting a criteria to be used for judging the amount of water drops on the plate, judging means for judging the amount of water drops on the plate by comparing an output level from the setting means and an output level from the receiving means and updating means for updating the criteria by storing the output level from the wave receiving means.

7. A raindrop sensor providing on a plate, comprising:
   wave transmitting means associated with the plate to radiate elastic waves thereinto;
   a coupler interposed between the plate and the wave transmitting means, the coupler holding the wave transmitting means at a predetermined angle relative to the plate so that the elastic waves are transmitted while being repeatedly reflected in the plate so that the wave transmitting means has a predetermined incident angle in relation to a normal of the plate, the incident angle of the elastic waves and a material of the holding means chosen so that a refractive angle of the elastic waves in the plate is an angle capable of only permitting transverse waves to enter into the plate; and
   wave receiving means associated with the plate to detect amplitude of the elastic waves transmitted in the plate.

8. A raindrop sensor provided on a window of a vehicle having an opaque coat, comprising:

wave transmitting means attached to the opaque coat to radiate elastic waves into the window;

holding means for holding the wave transmitting means at a predetermined angle relative to the window so that the elastic waves are transmitted while being repeatedly reflected in the window; and wave receiving means attached to the window to detect amplitude of the elastic waves transmitted in the window.

9. A raindrop sensor according to claim 8, wherein the wave receiving means is spaced apart a predetermined distance from the wave transmitting means on the opaque coat.

* * * * *